United States Patent
Chen et al.

(10) Patent No.: US 6,941,811 B2
(45) Date of Patent: Sep. 13, 2005

(54) METHOD AND APPARATUS FOR DETECTING WAFER FLAW

(75) Inventors: Chih-Kun Chen, Pa Te (TW);
Yao-Hsiung Kung, Hsien (TW); Tun Yuan Lo, Chung Li (TW)

(73) Assignee: Nan Ya Technology Corporation (TW)

( * ) Notice: Subject to any disclaimer, the term of this patent is extended or adjusted under 35 U.S.C. 154(b) by 56 days.

(21) Appl. No.: 10/633,414

(22) Filed: Aug. 4, 2003

(65) Prior Publication Data

US 2005/0028594 A1 Feb. 10, 2005

(51) Int. Cl.$^7$ .............................................. G01N 29/10
(52) U.S. Cl. ............................ 73/629; 73/627; 73/628
(58) Field of Search ......................... 73/597, 598, 599, 73/600, 602, 618, 620, 624, 625, 627, 628, 629

(56) References Cited

U.S. PATENT DOCUMENTS

| | | | | | |
|---|---|---|---|---|---|
| 4,366,716 | A | * | 1/1983 | Yoshida | 73/718 |
| 4,741,212 | A | * | 5/1988 | Rehwald | 73/600 |
| 4,768,155 | A | * | 8/1988 | Takishita et al. | 702/39 |
| 6,062,084 | A | * | 5/2000 | Chang et al. | 73/601 |
| 6,356,346 | B1 | * | 3/2002 | Hagen et al. | 356/237.1 |
| 2004/0024320 | A1 | * | 2/2004 | Karasawa et al. | 600/459 |

* cited by examiner

*Primary Examiner*—Hezron Williams
*Assistant Examiner*—Rose M. Miller
(74) *Attorney, Agent, or Firm*—Birch, Stewart, Kolasch & Birch, LLP

(57) ABSTRACT

The present invention provides an apparatus for detecting flaws in a wafer. The apparatus has a detection platform for holding a wafer positioned thereon, a cross-bar ultrasonic detection device positioned above the detection platform for emitting and receiving an ultrasonic wave reflected by a wafer; and a microprocessor for processing the reflected ultrasonic and transmits to a monitor.

19 Claims, 5 Drawing Sheets

METHOD AND APPARATUS FOR DETECTING WAFER FLAW

BACKGROUND OF THE INVENTION

1. Field of the Invention

The present invention relates to an apparatus and a method for detecting flaws in a silicon wafer, such as scratches on surface thereof, chips on edges thereof, or flaws inside the wafer.

2. Description of the Prior Art

In the fabrication of electronic devices, semi-conducting silicon material in the form of wafers is most frequently used for forming electronic circuits in a miniature scale. In the processing of electronic wafers, the wafer surface need multi processes for gaining a well planarization so as to satisfy the requirement of integrated circuit processing. The last procedure is wafer polishing, sometime the wafer will broken during the process. That will spend much time to clean the broken material on the machine platform, not only waste the process material, but also delay the manufacturing speed.

The reasons of wafer broken are usually due to some defects caused by preceding processes. In prior art, the wafer is usually immediately washed following the preceding process. After washing, checking if the wafer has any chip, scratch, or pollution by visual inspection, then proceeding with the wafer polishing. However, the traditional visual inspection cannot detect the flaws inside the wafer.

In the traditional technology of detecting, after the electronic wafer finished, using an optical microscope with chemical solution for inspecting the scratch, or using X-ray machine for inspecting structure flaws. However that equivalent is very expansive and spending much time. If using that for inspecting the wafer flaws before wafer polishing, that not fit the manufacturing efficiency and cost.

If there is an apparatus or method could sift the abnormal wafer out immediately and quickly before wafer polishing so as to reduce the wafer broken during manufacturing, the invention is desired.

SUMMARY OF THE INVENTION

An object of the present invention is to provide a detecting apparatus that can sift the abnormal wafer out immediately and quickly before wafer polishing beforehand so as to reduce the wafer broken during manufacturing.

In order to achieve the above objects, the present invention provides an apparatus for detecting flaws in a wafer. The apparatus comprises a detection platform for holding a wafer positioned thereon, a cross-bar ultrasonic detection device positioned above the detection platform for emitting and receiving an ultrasonic wave reflected by a wafer; and a microprocessor for processing the reflected ultrasonic and transmits to a monitor.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
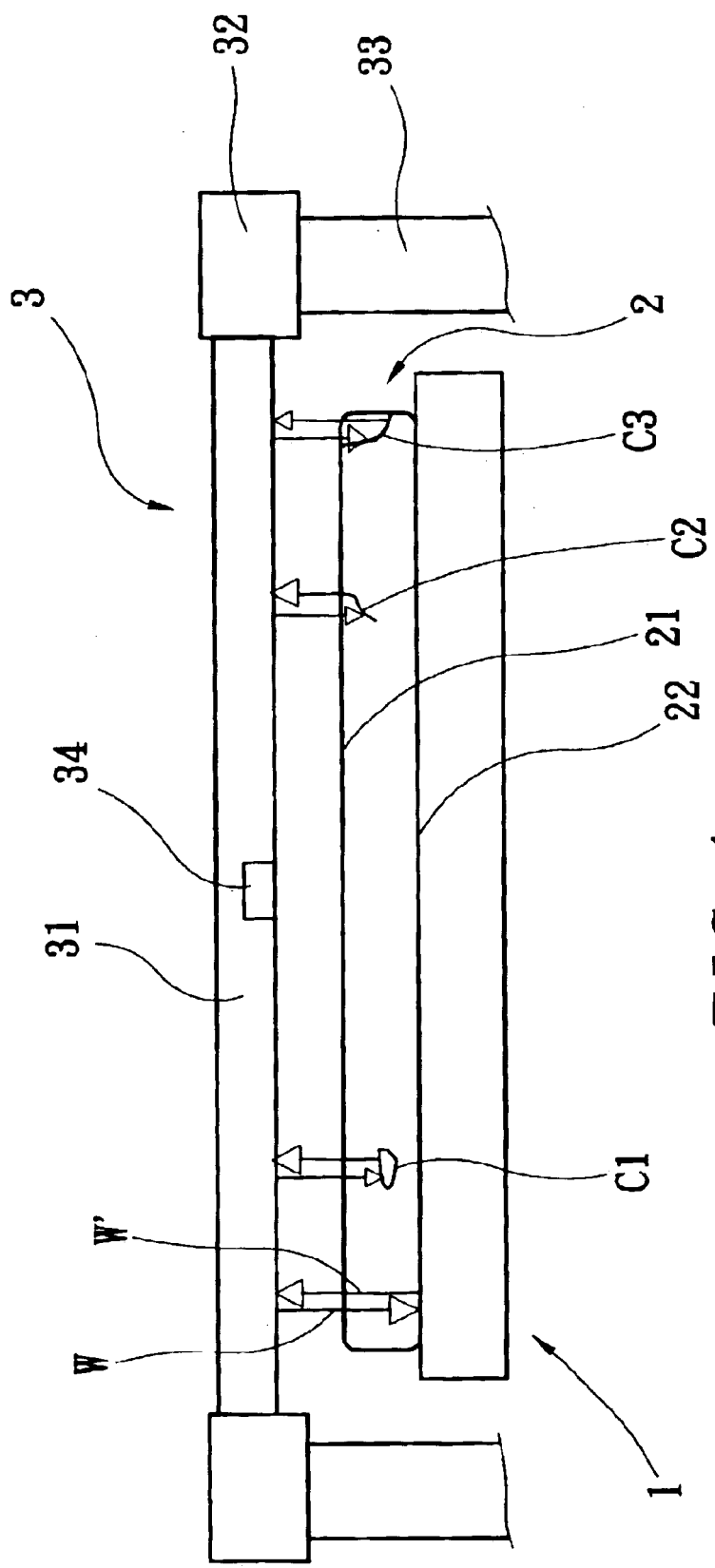
FIG. 1 is a perspective view according to the present invention.

Referring to the FIG. 1, which is a perspective view according to the present invention. The apparatus for detecting flaws in a wafer has a detection platform 1 for holding a wafer 2 positioned thereon. A cross-bar ultrasonic detection device 3 is positioned above the detection platform 1 for emitting an ultrasonic wave W and receiving an ultrasonic wave W' reflected by the wafer 2. The ultrasonic detection device 3 has a transducer 31 which is positioned above the detection platform 1. A pair of connecting units 32 are respectively connected with two ends of the transducer 31. A pair of supporting portions 33 are respectively connected with the connecting units 32. The transducer 31 has an emitting portion and a receiving portion for emitting a plane ultrasonic wave W to pass through a upper surface 21 of the wafer 2 and receiving a reflected wave W' from a bottom surface of the wafer 2 or flaws C1, C2, or C3 in the wafer 2. Wherein the emitting portion and-the receiving portion are mounted in the same side and are received in the transducer 31.

Figure 2:
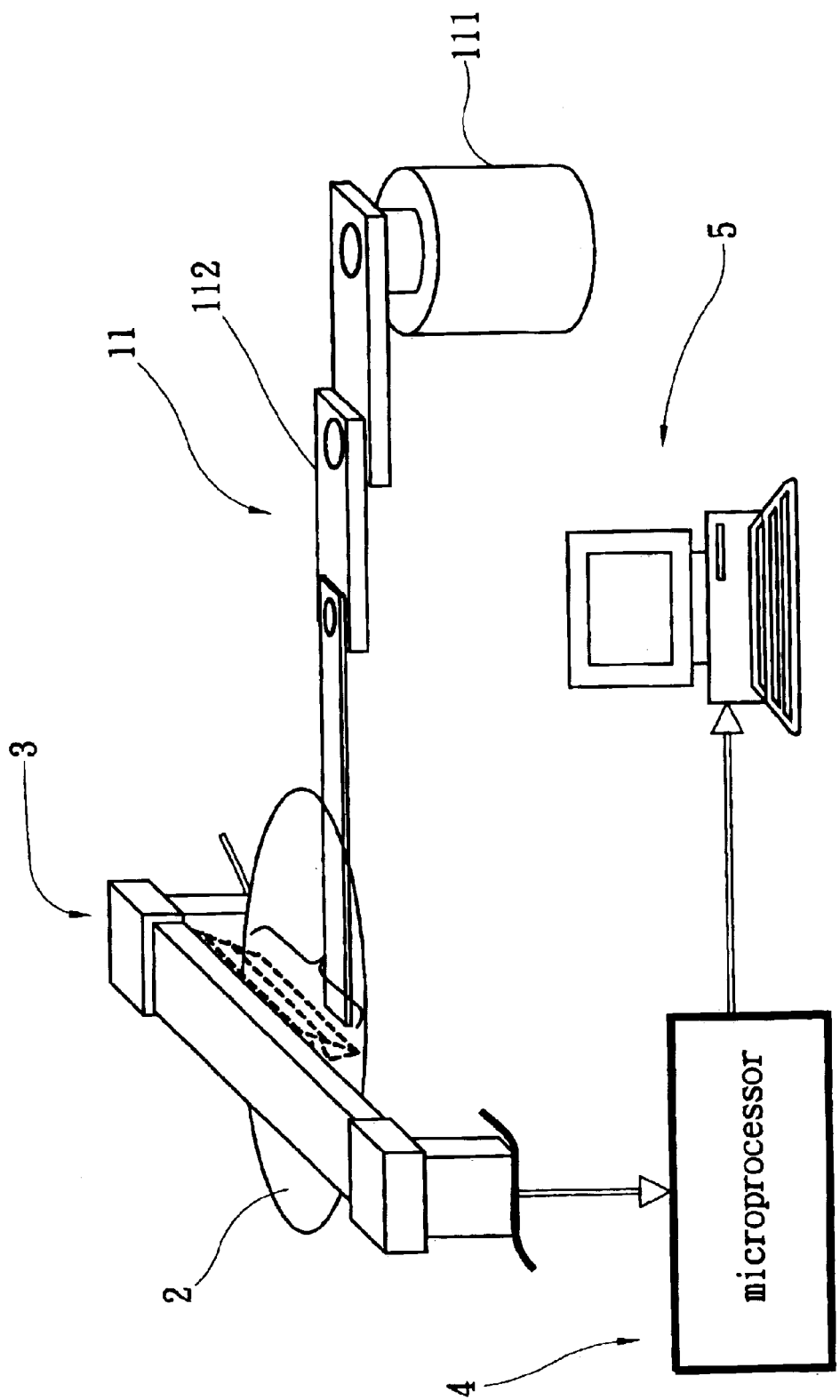
FIG. 2 is a perspective view according to the present invention with a robot arm.

Referring to the FIG. 2, which is an embodiment of the present invention, an apparatus for detecting flaws in a wafer with a robot arm. The detecting platform 1 can be a robot arm 11. The robot arm 11 has a driven motor 111, and a plurality of blades 112 for drawing or holding the wafer 2 and transporting an under place of the ultrasonic detection device 3. A microprocessor 4 is used to receive a message from the ultrasonic detection device 3 and process the message, then transmit the message to a monitor 5 for the users observing.

Figure 3:
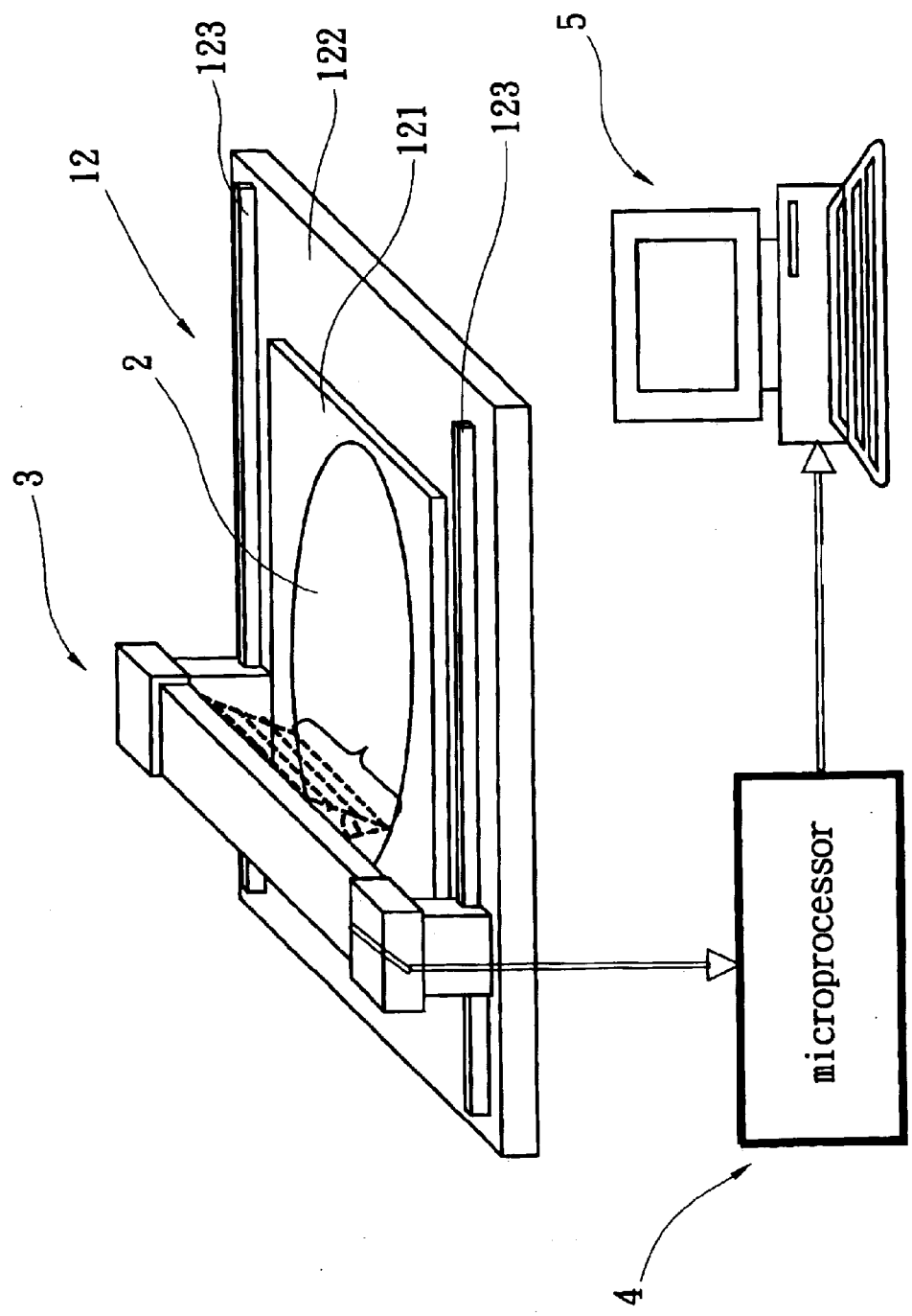
FIG. 3 is a perspective view according to the present invention with a chamber-module detecting platform.

Referring to the FIG. 3, which is another embodiment of the present invention. Wherein the detection platform 1 can be a chamber-module detection platform 12. The chamber-module detection platform 12 has a pad 121 for carrying the wafer 2, a table 122 for loading with the pad 121, and a pair of guiding track 123 for guiding the ultrasonic detection device 3 to scan the wafer 2.

When the reflected ultrasonic wave W' is abnormal, the microprocessor 4 will beep for reminding the operator, and stop scanning and moving out the wafer 2. The ultrasonic detection device 3 further has a sensor 34 mounted in the transducer 31 or in the supporting units 33 for sensing an incoming and outgoing of the wafer 2 and transmitting a begging message S or an end message E to the microprocessor 4 (referring to the FIG. 4). According to the message transmitted to the microprocessor 4, determining to start or stop scanning the wafer 2.

The operating principle of the present invention is as followed: the ultrasonic detecting is utilizing the character that a material can propagate, absorb, and reflect elastic waves for detecting flaws in a substrate. The transducer 31 has piezoelectric effect that can transfer a voltage pulse to a stress pulse and shoot into a substrate. The oscillation frequency that is larger than one hundred thousand hertz belongs to the scope of ultrasonic. For a thinner material, the ultrasonic speed V is equal to $\sqrt{(Eg/\rho)}$, wherein E is Young's modulus, g is gravity acceleration, and $\rho$ is density. Thereby get the ultrasonic speed in a wafer.

The present invention utilizes the method of pulse reflection, when a pulse is emitted and passing through substrate, the other surface will produce a reflected pulse and transmit to the transducer 31. Utilizing a time difference to time a velocity of sound, then getting twofold depth of the substrate. If the sound waves hit a discontinue interface when propagating, some will reflect. In that time, the monitor 5 will show a pulse of short time, so that it can get the position of the flaw. Continually move the transducer 31 for scanning and detecting, it can further decide a range of the flaw.

Figure 4:
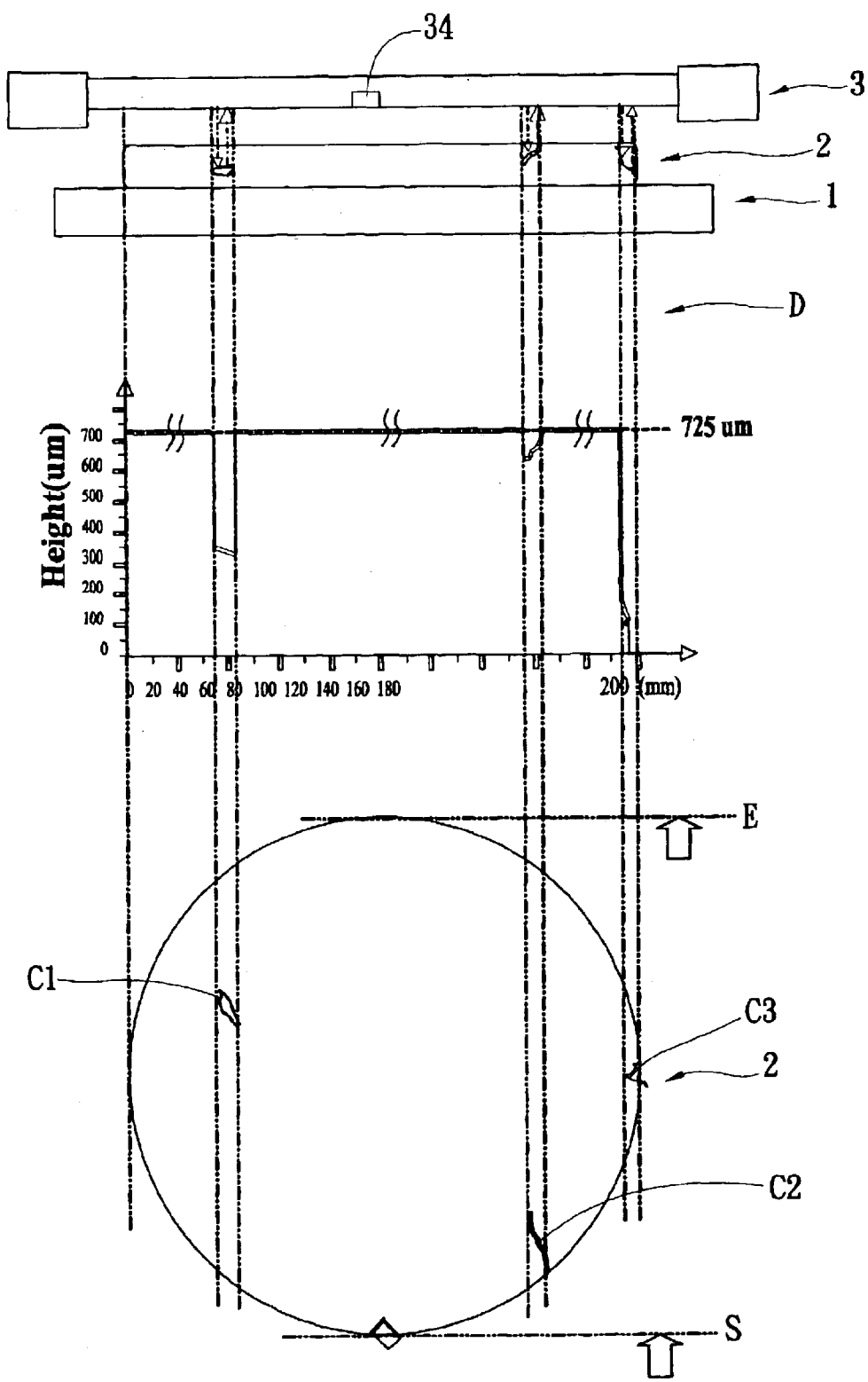
FIG. 4 is a perspective view and a detecting oscillogram according to the present invention.

Referring to the FIG. 4, which is a perspective view and a detecting oscillogram according to the present invention. Suppose the wafer has three kinds of flaws, respectively are first condition with an internal flaw C1, second condition with a surface scratch C2, and third condition with an edge chip C3. When the transducer 31 respectively receives the three kinds of reflected waves, just comparing with the normal reflected wave from the bottom surface and getting the time difference, then times with the speed of ultrasonic wave so as to get twofold depth of the flaw and show on the detecting oscillogram D.

Figure 5:
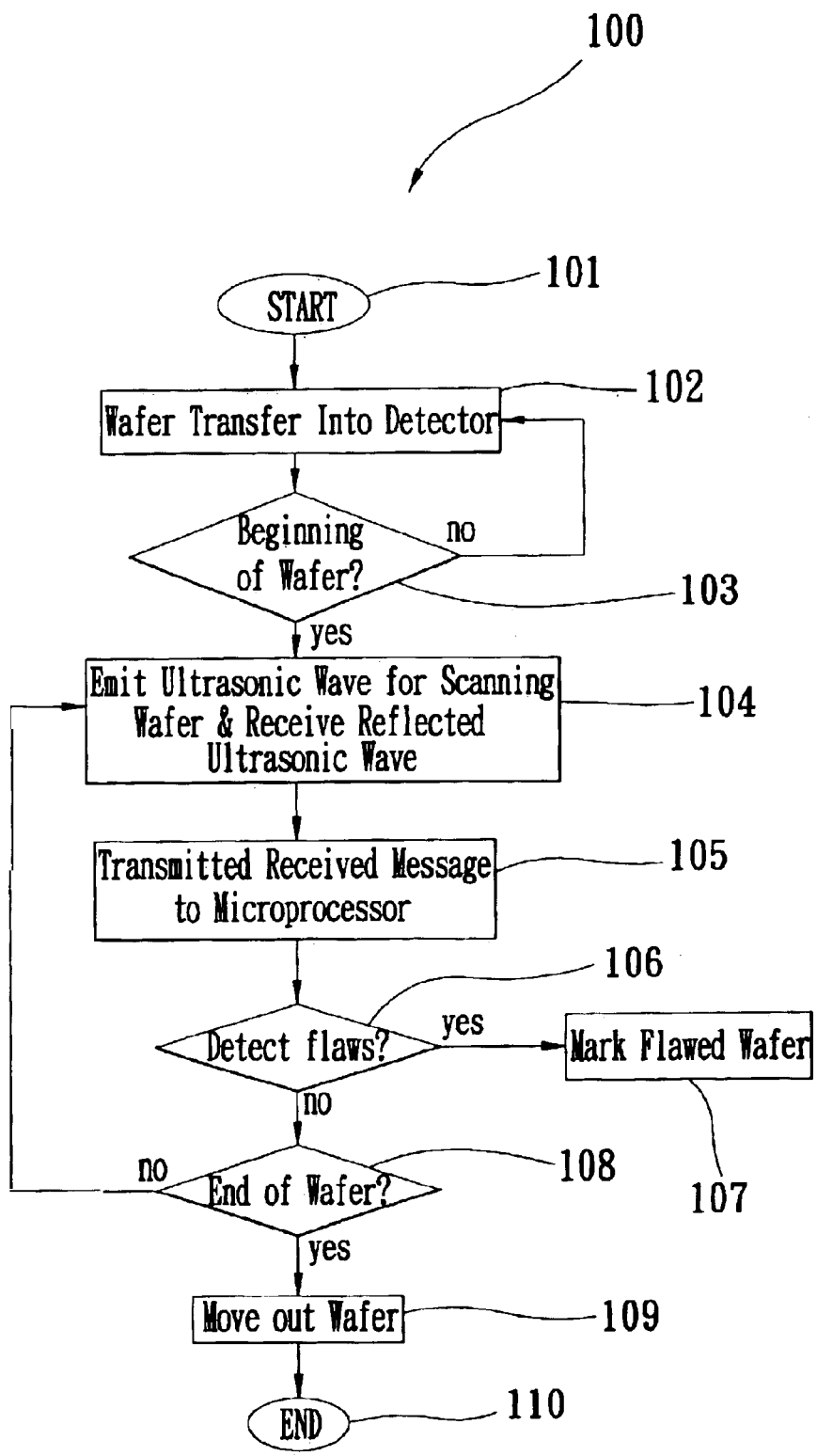
FIG. 5 is a process flow chart for the present invention method of detecting flaws in a wafer.

Referring the FIG. 5, which is a process flow chart for the present invention method of detecting flaws in a wafer. In the operation method 100, at the start 100 of the process, take out a wafer. At the step 102, the wafer is transferred into a detecting device 3. At the step 103, a sensor 34 mounted in the detecting device 3 inspects if it is a beginning of the wafer 2. If the wafer 2 has being transferred into the detecting device 3, then start to scan the wafer 2. If the wafer 2 has not being transferred into the detecting device 3, then still waiting for the wafer 2 and not start to scanning. At the step 104, which is following the step 103 with a beginning message, the detecting device 3 emits an ultrasonic wave W for scanning the wafer 2 and receiving the reflected ultrasonic wave W' from the wafer 2. At the step 105, the reflected ultrasonic waves W' are transmitted to a microprocessor for processing and determining if the wafer 2 has any flaw. At the step 106, if the wafer 2 has any abnormal reflected message, then the wafer 2 is marked at the proper location in step 107 and beeps a warning sound. If no flaws are found in the wafer 2, the next step 108 is sensing if the wafer 2 is transferred to an end thereof. If the wafer 2 has not been transferred to the end thereof, then go to the step 104 and continue to scan the wafer 2. If the wafer 2 has been transferred to the end thereof, the wafer 2 is transported out in the step 109. The detection process ends at step 110.

Therefore via the present invention, it provides a detecting apparatus and method that can sift the abnormal wafer out immediately and quickly before wafer polishing beforehand so as to reduce the wafer broken during manufacturing. It is really can increase the manufacturing efficiency and good rate.

While the present invention has been particularly shown and described with reference to particular embodiments thereof, it will be understood by those skilled in the are that various changes in from and details may be effected therein without departing from the spirit and scope of the invention as defined by the appended claims.

What is claimed is:

1. An apparatus for detecting flaws in a wafer comprising:
   a detection platform holding a wafer thereon for detecting;
   a cross-bar ultrasonic detection device positioned above said detection platform for emitting and receiving an ultrasonic wave reflected by the wafer, a width of said ultrasonic detection device being wider than or equal to a radius of said wafer; and
   a microprocessor for processing said reflected ultrasonic and transmitting to a monitor; whereby detecting flaws in said wafer.

2. The apparatus for detecting flaws in a wafer according to claim 1, wherein said detection platform is a robot arm for holding and drawing said wafer.

3. The apparatus for detecting flaws in a wafer according to claim 1, wherein said detection platform is a chamber-module detection platform having a pad for carrying said wafer, and a table for carrying said pad.

4. The apparatus for detecting wafer flaw according to claim 3, wherein said pad is formed with a pair of guiding tracks for guiding said ultrasonic detection device.

5. The apparatus for detecting flaws in a wafer according to claim 1, wherein said ultrasonic detection device has a transducer positioned above said detection platform, and a pair of supporting portion connected with two ends of the transducer, said transducer having an emitting portion and a receiving portion mounted therein.

6. The apparatus for detecting flaws in a wafer according to claim 5, further comprising a sensor mounted in the transducer or the supporting portions for sensing an incoming and outgoing of said wafer and transmitting a beginning or end message to said microprocessor.

7. An apparatus for detecting flaws in a wafer according to claim 1, wherein frequencies of said ultrasonic wave emitted by said ultrasonic detection device are between one hundred million and five thousands million hertz.

8. A method for detecting flaws in a wafer comprising the steps of:
   providing a detection apparatus which comprises a detection platform for holding a wafer thereon, a cross-bar ultrasonic detection device positioned above said detection platform, and a microprocessor, a width of said ultrasonic detection device being wider than or equal to a radius of said wafer;
   emitting an ultrasonic wave toward a surface of said wafer and receiving a reflected wave from a bottom or a flaw in said wafer;
   transmitting said reflected ultrasonic wave to said microprocessor and processing said reflected ultrasonic wave;
   determining if said wafer has any flaw for marking the flawed wafer via said microprocessor; and
   providing a sensor for inspecting if said wafer is transferred to an end thereof for controlling a detecting sequence.

9. A The method for detecting flaws in a wafer according to claim 8, further comprising the step of beeping when detecting said wafer has flaw.

10. The method for detecting flaws in a wafer according to claim 8, wherein said cross-bar ultrasonic detection device is positioned above said wafer.

11. The method for detecting flaws in a wafer according to claim 8, wherein said ultrasonic detection device has an emitting portion and a receiving portion mounted therein.

12. An apparatus for detecting flaws in a wafer comprising:
   a detection platform holding a wafer thereon for detecting;
   a cross-bar ultrasonic detection device positioned above said detection platform for emitting an plane ultrasonic wave and receiving the ultrasonic wave reflected from the wafer; and a microprocessor for processing said reflected ultrasonic and transmitting to a monitor; whereby detecting flaws in said wafer.

13. The apparatus for detecting flaws in a wafer according to claim 12, wherein said detection platform is a robot arm for holding and drawing said wafer.

14. The apparatus for detecting flaws in a wafer according to claim 12, wherein said detection platform is a chamber-module detection platform having a pad for carrying said wafer, and a table for carrying said pad.

15. The apparatus for detecting wafer flaw according to claim 14, wherein said pad is formed with a pair of guiding tracks for guiding said ultrasonic detection device.

16. The apparatus for detecting flaws in a wafer according to claim 12, wherein said ultrasonic detection device has a transducer positioned above said detection platform, and a pair of supporting portion connected with two ends of the transducer, said transducer having an emitting portion and a receiving portion mounted therein.

17. The apparatus for detecting flaws in a wafer according to claim 16, further comprising a sensor mounted in the transducer or the supporting portions for sensing an incoming and outgoing of said wafer and transmitting a beginning or end message to said microprocessor.

18. The apparatus for detecting flaws in a wafer according to claim 12, wherein frequencies of said ultrasonic wave emitted by said ultrasonic detection device are between one hundred million and five thousands million hertz.

19. The apparatus for detecting flaws in a wafer according to claim 12, wherein a width of said ultrasonic detection device is wider than or equal to a radius of said wafer.

* * * * *